United States Patent [19]

Schmukler et al.

[11] Patent Number: 5,286,432
[45] Date of Patent: Feb. 15, 1994

[54] FABRICATION OF MICRON-RANGE HOLES IN PROTECTIVE BARRIERS AND ENCAPSULATING MATERIALS

[76] Inventors: Robert Schmukler, 13905 Vista Dr., Rockville, Md. 20853; Richard B. Beard, 21 Willow Way, Atco, N.J. 08004; Frederick C. Prout, 937 Wesley Ave., Huntingdon Valley, Pa. 19006

[21] Appl. No.: 859,778

[22] Filed: Mar. 30, 1992

[51] Int. Cl.$^5$ .............................................. B29D 19/08
[52] U.S. Cl. ...................................... 264/155; 264/28; 264/163; 264/291; 264/348
[58] Field of Search ................. 264/28, 40.1, 154, 155, 264/156, 163, 291, 292, 340, 348; 83/15, 18, 175, 452

[56] References Cited

U.S. PATENT DOCUMENTS

| | | | |
|---|---|---|---|
| 2,532,739 | 12/1950 | Slusher | 83/175 |
| 2,612,950 | 10/1952 | Ewing | 83/175 |
| 2,860,532 | 11/1958 | Zickafoose | 408/91 |
| 3,117,479 | 1/1964 | Bisbis | 83/308 |
| 3,508,760 | 4/1970 | Woodling | 264/154 |
| 3,688,386 | 9/1972 | Pereira | 264/155 |
| 3,818,789 | 6/1974 | Vargo | 83/175 |
| 4,059,120 | 11/1977 | Molins et al. | 73/1 R |
| 4,112,795 | 9/1978 | de Putter | 83/170 |
| 4,527,988 | 7/1985 | Lutz et al. | 604/349 |
| 4,655,986 | 4/1987 | Cothran et al. | 264/154 |
| 4,964,992 | 10/1990 | Goldsmith | 264/49 |
| 5,122,390 | 6/1992 | Rearick et al. | 427/117 |
| 5,138,871 | 8/1992 | Retta et al. | 73/40.7 |

FOREIGN PATENT DOCUMENTS

| | | | |
|---|---|---|---|
| 0407368 | 1/1991 | European Pat. Off. | |
| 97068 | 12/1896 | Fed. Rep. of Germany | |
| 2215300 | 1/1973 | France | 264/155 |
| 55-5861 | 1/1980 | Japan | 264/154 |
| 58-20416 | 2/1983 | Japan | 264/28 |
| WO92/00798 | 1/1992 | PCT Int'l Appl. | 264/154 |
| 263865 | 12/1966 | U.S.S.R. | 264/155 |

*Primary Examiner*—Jay H. Woo
*Assistant Examiner*—Robert B. Davis
*Attorney, Agent, or Firm*—Lowe Price LeBlanc & Becker

[57] ABSTRACT

A method of fabricating micron-range holes in elastic barrier materials which involves securing an elastic barrier material to a restraining ring and removing a limited portion of the elastic barrier material so as to form a hole having a diameter of less than 0.5 to 10 μm. The portion of the elastic barrier material which is removed may be removed by a drilling, punching or clipping process.

24 Claims, 3 Drawing Sheets

FABRICATION OF MICRON-RANGE HOLES IN PROTECTIVE BARRIERS AND ENCAPSULATING MATERIALS

TECHNICAL FIELD

The present invention relates to the detection of manufacturing defects or holes in barrier materials, such as condoms and rubber gloves. In particular, the present invention relates to the fabrication of micron-range calibration holes in protective barriers and encapsulating materials to provide known standards for hole detection tests.

BACKGROUND ART

The ability to evaluate new designs and/or improve existing instruments and methodologies for the detection of manufacturing defects or holes in barriers, such as condoms and rubber gloves, is dependent on calibration (hole) standards. The production of these calibration standards to evaluate test instruments requires the ability to produce small holes (1–10 μm diameter) in intact condoms and rubber gloves. Hole calibration standards allow a quantitative comparison between different tests or between existing and improved tests.

Fabricating hole standards in an elastic polymer such as latex, the prevalent condom and glove material, is a difficult task due to the high elasticity of latex. When a simple pin is used to create a hole in a latex film, the usual result is a closed hole or very large hole (a result of shear or tearing) under conditions of zero strain (normal size). This results from the sharp point first piercing the material, followed by the larger diameter pin shank stretching the small perforation as the pin is advanced through the material. In addition, a 1–10 μm diameter hole in a normal condom/glove (thickness 50–90 μm/100–250 μm) results in a range of aspect ratios (length/diameter) of 5–90 for condoms and 10–250 for gloves. Producing a hole with aspect ratios greater than 10 at these size diameters is difficult. Tooling, for fabricating holes, with these aspect ratios and these small diameters does not exist and barrier materials of interest tend to be too flexible for tooling and not normally sufficiently rigid for punching or drilling holes.

The use of eximer (Ultraviolet(UV)) lasers has also been tried as a way of producing holes. However, latex (and most polymers) are degraded by UV light. Latex that has an eximer irradiated hole is usually carbonized the hole. Even when the intensity of the eximer laser is reduced, the latex surface is altered chemically by the laser irradiation. A hole, whose walls and outer surrounding surface is chemically different from bulk material, will exhibit different physical properties and behavior. Therefore, a hole made in this way will not be a good representation of a naturally occurring defect, whose properties should closely resemble that of the bulk or intact material.

DISCLOSURE OF THE INVENTION

It is one object of the present invention to provide a method of producing holes in barrier materials.

Another object of the present invention is to provide a method of producing calibration holes in barrier materials.

It is another object of the present invention to provide a method of producing holes in elastic barrier materials.

A further object of the present invention is to provide a method of producing calibration holes in elastic barrier materials.

It is a further object of the present invention to provide a method of drilling holes in barrier materials.

A still further object of the present invention is to provide a method of punching holes in barrier materials.

A still further object of the present invention is to provide a method of clipping holes in barrier materials.

An even further object of the present invention is to provide a method of producing holes in viscoelastic materials.

According to these and further objects of the present invention which will become apparent as the description thereof is presented below, the present invention provides a method of fabricating micron-range holes in elastic barrier materials which comprises:

securing an elastic barrier material to a restraining ring; and removing a limited portion of the elastic barrier material so as to form a hole having a diameter of less than 0.5 to 10 μm.

BRIEF DESCRIPTION OF DRAWINGS

The present invention will hereafter be described with reference to the attached drawings which are given by way of non-limiting examples only, in which.

BEST MODE FOR CARRYING OUT THE INVENTION

A method for producing holes in barrier materials that are intended to be hole detection test standards, needs to meet two basic criteria: (1) the chemical and physical properties of the barrier material surrounding the hole should be minimally altered from the chemical and physical properties of bulk material; and (2) the hole should exist at zero strain and zero stress, since this is approximately the state under which these barriers are used and expected to provide protection. When these criteria are met, reasonable assurances can be given that the artificially produced holes will resemble natural manufacturing defects.

There are three different methods for producing sub-10-micron or larger holes in barrier materials that have been developed during the course of the present invention: (1) drilling of holes in frozen barrier materials; (2) punching holes in cooled or room temperature barrier materials; and (3) clipping holes in barrier materials at ambient temperatures. All of these methods have in common the removal of a small amount or limited portion of the barrier material.

During the course of the present invention, it has been discovered that the chemical and physical behavior of latex appears to be unchanged when the latex is first cooled to the temperature of liquid nitrogen ($-196°$ C.) and subsequently rewarmed to ambient temperature. The physical behavior of latex (and other natural and synthetic polymers and rubbers) at temperatures both below and near the glass transition temperature interval ($T_g$) is markedly different from its physical behavior at room temperature. The properties of latex near its $T_g$ ($= -70°$ C.) are more leathery and rubbery. At temperatures well below $T_g$, latex is quite brittle and glass-like.

Another property that latex shares with other natural and synthetic polymers and rubbers is that the retractive force (elastic modulus) of the polymer increases with increasing temperature and decreases with decreasing temperatures. This behavior is opposite that of metals and produces an expansion of the surface area of thin barrier materials upon cooling. Removal of material from this type of barrier material in a cooled and expanded state will produced a smaller-sized hole upon rewarming. First stretching the barrier at ambient temperature, and then cooling before removal of material to form a hole, can produce, in the stretched barrier, at ambient temperature, a hole whose size is equal to the diameter of the removal tool. Relaxation (unstretching) of the barrier will then result in a hole of reduced size at zero strain. The present invention takes advantage of the changes in material properties with temperature of elastic barrier materials, such as latex, which provides optimal conditions for producing micron-sized holes.

Figure 2A:
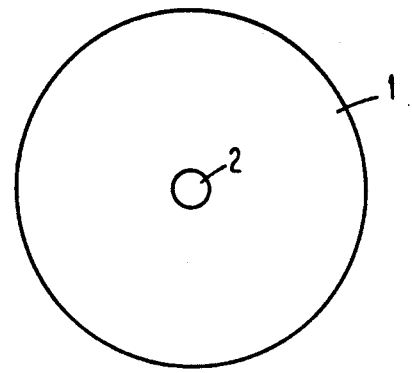
FIGS. 2A–2B depict the manner in which the barrier material in FIGS. 1A–1D is uniformly stretched prior to producing a hole therein.

The first method of producing micron-sized holes in barriers materials according to the present invention involves freezing the barrier material, e.g., latex with a suitable liquified gas such as liquid nitrogen and then drilling a hole using a conventional 50–100 $\mu$m (0.002–0.004") drill. As shown in FIG. 2A, the barrier material 1 is first marked with a circle 2 using a marking pen in the area where a hole is to be produced.

Figure 1A:
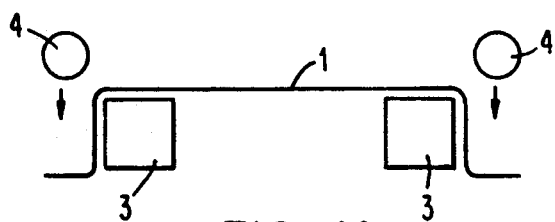
FIGS. 1A–1D depict the manner in which holes are produced in a barrier material according to one embodiment of the present invention.
Figure 1B:
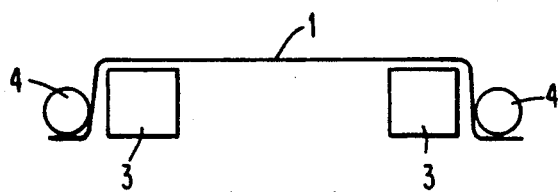
Figure 1C:
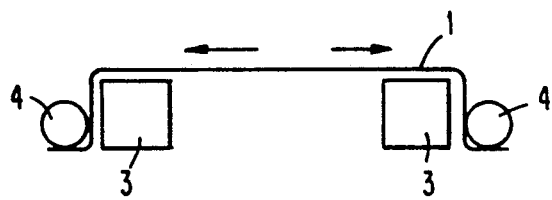
Figure 2B:
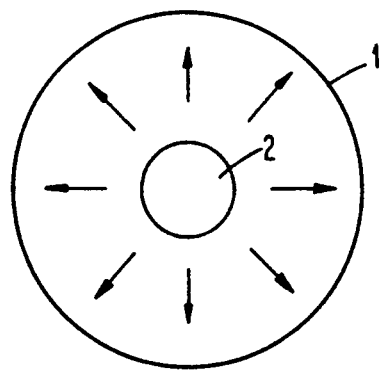

The marked area is centered on a plastic (i.e., Delrin) restraining ring 3 as shown in FIG. 1A and secured with one or more soft o-rings 4, like a drum head, as shown in FIG. 1B. After the barrier material 1 is secured to the restraining ring 3, the diameter of the marked circle 2 is measured, then the marked circle 2 is carefully enlarged uniformly as shown in FIG. 2B by radially stretching the barrier material 1 (FIG. 1C) to achieve the desired amount of strain.

Figure 1D:
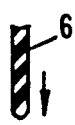
Figure 1D:
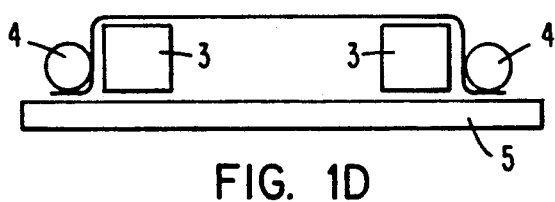

After the barrier material 1 is stretched, it is placed on a pedestal 5 for support (FIG. 1D), which is submerged in a liquid nitrogen filled reservoir (not shown). Once the barrier material 1 is cooled to $-196°$ C., a hole can then be drilled using a commercially available drill bit 6 (FIG. 1D). The amount of stretching needed will depend on the thickness and elasticity of the barrier material 1. The amount of stretching can easily be adjusted to achieve a desired unstressed hole size. Hole sizes between 2–5 $\mu$m have been achieved in this manner.

Figure 3:
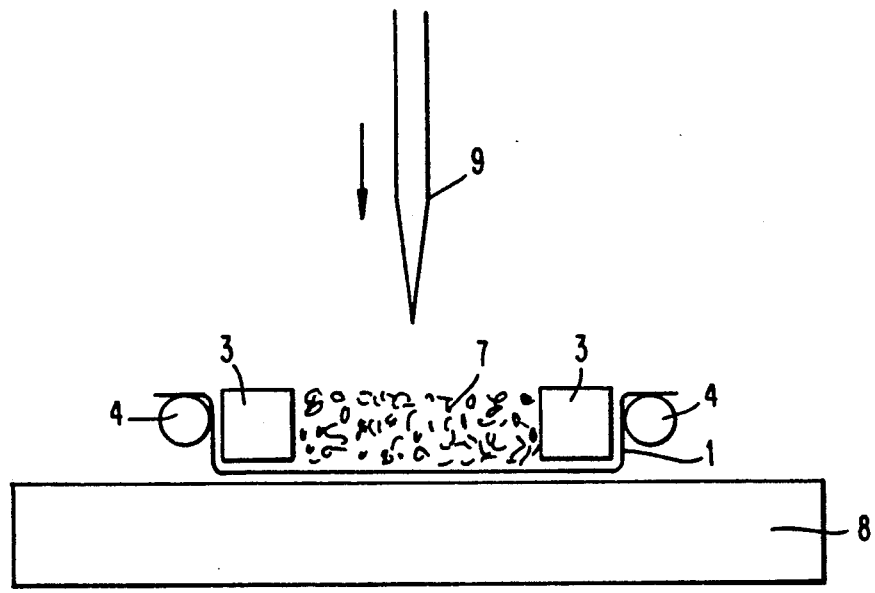
FIG. 3 depicts the manner in which holes are produced in a barrier material according to another embodiment of the present invention.

The second method of making micron-sized holes in barrier materials according to the present invention involves punching holes in the barrier materials in either a stretched or unstretched state. The first embodiment of the second method shares some aspects with the first method described above in reference to FIGS. 1A–1D and 2A–2B. In the first embodiment of this method, the barrier material 1, e.g. latex, is prepared identically with the first method, up to the placement of the supported, stretched barrier material in the liquified gas. In this embodiment, after the barrier material 1 is secured on the restraining ring 3, the restraining ring 3 is inverted to form a cup-like configuration shown in FIG. 3. After being inverted, the restraining ring 3 is carefully filled with ground dry ice (solid $CO_2$) 7, and placed on another piece of flat dry ice 8 for support. When the barrier material 1 has cooled to the temperature of dry ice ($-100°$ C.), a hole is then punched in the stiffened barrier materal 1 utilizing a commercial or natural punch 9, point first. (See FIG. 4B)

The punches which have been found to be useful for this embodiment of the present invention include miniature commercial steel punches or punches made from natural materials such as punches derived from plant spines, plant stickers, plant thorns, cactus needles, insect spines and animal spines, such as porcupine spines and sea urchin spines.

The key to hole fabrication using natural tools according to the present invention is the use of thin, tapered, needle-like structures which are naturally designed to pierce the skin or other biological visco-elastic materials, or tissues. According to the first embodiment of the second method, when using cactus needles from, for example, the Engleman family of prickly pear cacti, some tool preparation may be found to be beneficial. In the tooling preparation, the barbs, which point away from the tip, are carefully removed from the shank of the needle and the point was squared off to produce a cutting edge (a flat face with 90° corners) similar to commercial punches.

Stingers and spines from natural sources generally have shanks which taper down to a fine point for piercing. This point can be quite small in diameter, e.g., 5–10 $\mu$m as in the case of the Engleman family of cacti. The mechanical strength of punches derived from natural sources have surprisingly been found to be so high that further reduction in shank diameter near the tip is possible during tool preparation, if desired.

The use of poison or venom stingers, for example from bees and wasps, can be used according to the present invention to produce hollow punches that provide a space in which the punched out material can be received. According to the present invention it has been found hollow punches produced from poison or venom stingers can be utilized to produce holes which have more uniform cross sectional diameters. Holes having diameters in the range of 2–4 $\mu$m have been produced using hollow punches produced from poison or venom stingers according to the present invention.

The second embodiment of the second method, using the natural-fiber-punch approach for making micron-sized holes at ambient temperature as shown in FIG. 4, involves the use of a cactus needle 10 backwards. Preparation of the cactus needle 10, as discussed above, is not necessary in this embodiment. The barrier material 1 is first marked, then mounted on the restraining ring 3 and stretched, as in the two previously described procedures. According to one method, the larger diameter of the conically shaped needle 1, rather than the tip, enters the latex barrier first. This needle may be clamped in a small drill press to facilitate controlled entry.

One feature of the Engleman family of cacti needles is their outer covering of barbs which point away from the point of the needle. These barbs make it possible according to the first embodiment of the second method to penetrate the barrier material 1 on the downstroke, and remove material from the side wall of the hole on the upstroke, when moved in the reverse direction (see direction arrows in FIG. 4B). The tiny barbs act like small cutters which chip away residual material left from the initial puncture.

When used in a manner in which the broken, or cut end of the needle, enters the barrier material first, no special preparation is needed. Needles may be used in the reverse direction punching in the same configuration as they are taken from the cactus. The needles are either broken from the cactus by twisting with a pair of pliers, or cut from the cactus with scissors. This produces a flat and slightly jagged surface on the face form base of the needle.

Figure 4A:
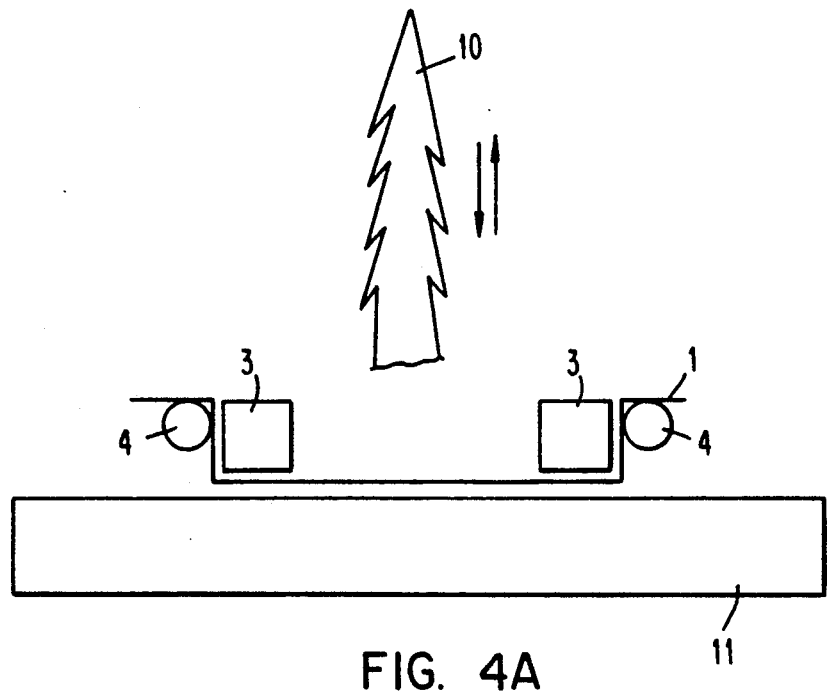
FIGS. 4A–4B depict the manner in which holes are produced in a barrier material according to a further embodiment of the present invention.
Figure 4B:
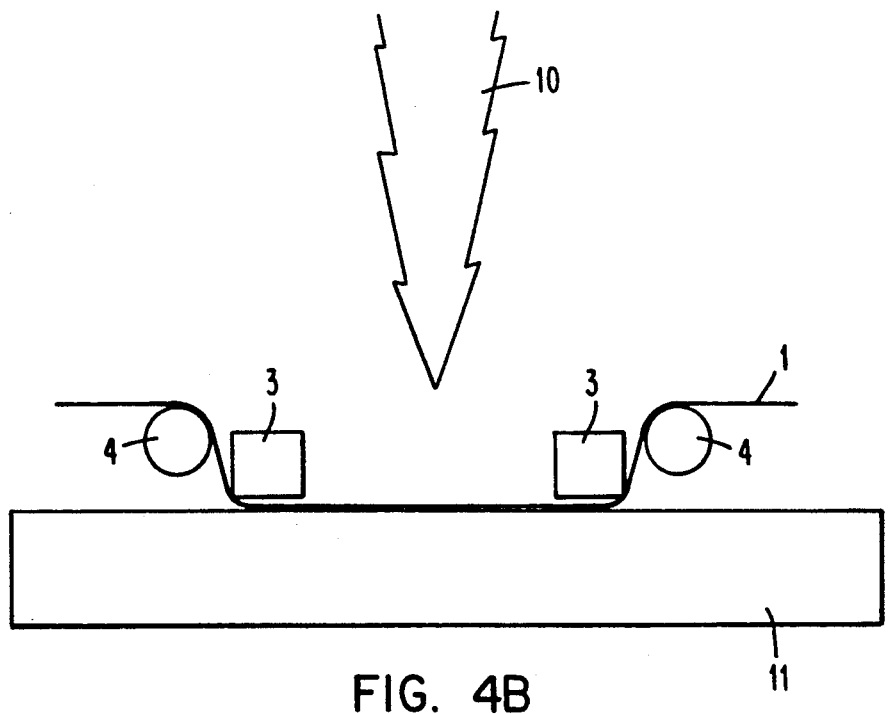

As shown in FIGS. 4A and 4B, this method and all other ambient temperature methods may be aided by backing the barrier material with a rigid support 11, e.g., styrofoam. The rigid support 11 should be sufficiently rigid to support the barrier material 1 and yet readily penetrable by the cactus needle 10. When utilizing a styrofoam support it has been found that the penetration process initially stretches the barrier material 1 between the cells of styrofoam. This stretching and subsequent cutting sequence consistently produces small holes. After the piercing and withdrawal of the needle, the stretched hole shrinks back to micron size. This process has been carried out successfully at ambient temperature, producing open holes in about one to ten micron range and beyond.

Figure 5:
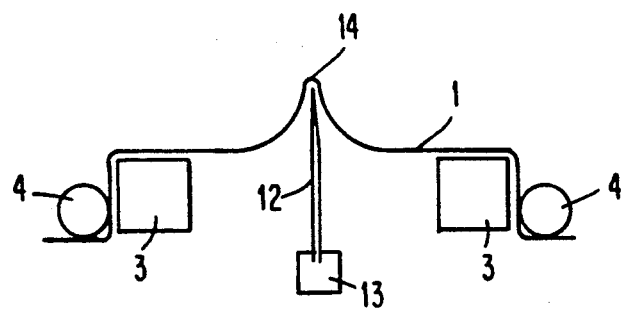
FIG. 5 depicts the manner in which holes are produced in a barrier material according to a further embodiment of the present invention.
Figure 6A:
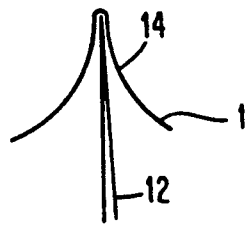
FIGS. 6A–6B depict the manner in which a hole is cut into the barrier material of FIG. 5.
Figure 6B:
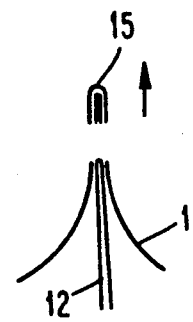

The last method for producing micron-sized holes according to the present invention as depicted in FIGS. 5 and 6A-6B involves removably clipping a small portion of the barrier material 1 at ambient temperatures. In this technique, the barrier material 1 is again marked with a circle and mounted on a restraining ring 3. However, in contrast to the methods discussed above, in this method, the barrier material 1 is not stretched radially. A cactus needle 12 or any other natural barb or stinger in its natural state, without any further preparation, is clamped in a support 13, e.g. vise. The marked circle on the flaccid barrier material 1 mounted on the restraining ring 3, is centered over the cactus needle 12, preferably using a stereo microscope. The restraining ring 3 is then gently pressed down onto the cactus needle 12 to produce a puckered peak 14 in the barrier material 1 of 5-8 mm height (FIG. 6A). A clipper or similar type of cutting tool (not shown) is then used to clip off the top of the cactus needle 12. This also removes a limited portion or small amount of the barrier material 15 covering the tip of the cactus needle 12, as shown in FIG. 6B, thereby producing a 1-4 $\mu$m hole.

The present invention has been found to be applicable to a variety of elastic barrier materials including both natural and synthetic polymers and rubbers. Examples of such materials include, but are not limited to, barriers including condoms, diaphragms, surgical gloves, dental dams, etc., which must be carefully tested periodically during their manufacture.

Application of the above-disclosed embodiments of the present invention is not limited to use in conjunction with elastic barrier materials. Examples of protective barriers include: latex and other polymer condoms, gloves, and diaphragms; metallized viscoelastic foils; and thin metallic foils. For example, the present invention can be used for fabricating holes in viscoelastic materials for use in processes other than those used as barrier materials.

The present method of producing micro-range holes can also be used to produce holes (e.g., 05-10 $\mu$m) in materials with surface tensions ranging from lyophobic to lyophilic interfaces in order to produce specific permability or porosity articles, such as selectively permeable barriers.

Although the invention has been described with reference to particular means, materials and embodiments, from the foregoing description, one skilled in the art can ascertain the essential characteristics of the present invention and various changes and modifications may be made to adapt the various uses and characteristics thereof without departing from the spirit and scope of the present invention as described in the claims which follow.

What is claimed is:

1. A method of fabricating micro-range holes in elastic barrier materials which comprises:
   securing an elastic barrier material to a restraining ring; and
   removing a limited portion of said elastic barrier material so as to form a hole having a diameter of less than about 10 $\mu$m in said elastic barrier material, said hole being defined by a surrounding portion of said elastic barrier material having a physical structure which is uniform throughout said elastic barrier material.

2. A method of fabricating micron-range holes in elastic barrier materials according to claim 1, wherein said elastic barrier material is stretched on said restraining ring prior to removing said limited portion of said elastic barrier material.

3. A method of fabricating micron-range holes in elastic barrier materials according to claim 2, wherein said limited portion of said elastic barrier is removed by punching said elastic barrier material with a tool.

4. A method of fabricating micron-range holes in elastic barrier materials according to claim 3, wherein said elastic barrier material is cooled to at least its glass transition temperature after being stretched and prior to removing said limited portion of said elastic barrier material.

5. A method of fabricating micron-range holes in elastic barrier materials according to claim 4, wherein said elastic barrier material is cooled below its glass transition temperature after being stretched and prior to removing said limited portion of said elastic barrier material.

6. A method of fabricating micron-range holes in elastic barrier materials according to claim 3, wherein said tool comprises a metal punch.

7. A method of fabricating micron-range holes in elastic barrier materials according to claim 3, wherein said tool is selected from the group consisting of plant spines, plant stickers, insect stingers, and animal spines.

8. A method of fabricating micron-range holes in elastic barrier materials according to claim 7, wherein said plant stickers are plant thorns and said animal spines are insect spines.

9. A method of fabricating micron-range holes in elastic barrier materials according to claim 8, wherein said plant thorns are cactus needles.

10. A method of fabricating micron-range holes in elastic barrier materials according to claim 8, wherein said tool is hollow.

11. A method of fabricating micron-range holes in elastic barrier materials according to claim 3, wherein said elastic barrier material is positioned on a support means.

12. A method of fabricating micron-range holes in elastic barrier materials according to claim 1, wherein said elastic barrier material is cooled below its glass transition temperature after being stretched and prior to removing said limited portion of said elastic barrier material.

13. A method of fabricating micron-range holes in elastic barrier materials according to claim 11, wherein said limited portion of said elastic barrier is removed by drilling said barrier material.

14. A method of fabricating micron-range holes in elastic barrier materials according to claim 2, wherein said limited portion of said elastic barrier is removed by punching said barrier material with a cactus needle having barbs which point toward a punching end of said cactus needle.

15. A method of fabricating micron-range holes in elastic barrier materials according to claim 1, wherein said limited portion of said elastic barrier is removed by clipping said limited portion of said elastic barrier material from said elastic barrier material.

16. A method of fabricating micron-range holes in elastic barrier materials according to claim 15, wherein said limited portion of said elastic barrier material is stretched prior to clipping by pressing a projecting element against said elastic barrier material.

17. A method of fabricating micron-range holes in elastic barrier materials according to claim 16, wherein said projecting element is selected from the group consisting of plant spines, plant stickers, insect stingers, and animal spines.

18. A method of fabricating micron-range holes in elastic barrier materials according to claim 1, wherein said elastic barrier material is selected from the group consisting of natural or synthetic polymers and rubbers, and metallic-coated viscoelastic membranes and thin metallic foils.

19. A method of fabricating micron-range holes in elastic barrier materials according to claim 13, wherein said hole has a diameter in the range of about 2 to 5 $\mu m$.

20. A method of fabricating micron-range holes in elastic barrier materials according to claims 2 or 7, wherein said hole has a diameter less than about 10 $\mu m$, and said material is removed by punching said barrier material with a barbed natural needle whose barbs point away from the punching end, or tip of the needle.

21. A method of fabricating micron-range holes in viscoelastic membranes which comprises:
   securing a viscoelastic membrane to a restraining ring; and
   removing a limited portion of said viscoelastic membrane so as to form a hole having a diameter of less than about 10 $\mu m$ in said viscoelastic membrane, said hole being defined by a surrounding portion of said viscoelastic membrane having a physical structure which is uniform throughout said viscoelastic membrane.

22. A method of producing a permeable barrier which comprises:
   securing a barrier material to a restraining ring; and
   removing limited portions of said barrier material so as to form holes having an average diameter of less than about 10 $\mu m$ in said barrier material, each of said holes being defined by a surrounding portion of said barrier material having a physical structure which is uniform throughout said barrier material.

23. A method of fabricating micron range holes in elastic barrier materials according to claim 17, wherein said plant stickers are plant thorns and said animal spines are insect spines.

24. A method of fabricating micron-range holes in elastic barrier materials according to claim 23, wherein said plant thorns are cactus needles.

* * * * *